United States Patent [19]

Omar

[11] Patent Number: 5,730,987
[45] Date of Patent: Mar. 24, 1998

[54] **MEDICATION FOR IMPOTENCE CONTAINING LYOPHILIZED ROE AND A POWDERED EXTRACT OF *GINKGO BILOBA***

[76] Inventor: Lotfy Ismail Omar, P.O. Box F396, Kew Gardens, N.Y. 11415

[21] Appl. No.: 660,875

[22] Filed: Jun. 10, 1996

[51] Int. Cl.⁶ .......................... A61K 35/78; A61K 35/54
[52] U.S. Cl. .................. 424/195.1; 424/561; 424/451; 424/641; 424/682; 424/702; 514/78
[58] Field of Search .................. 424/195.1, 561, 424/451, 641, 682, 702; 426/656; 514/78

[56] References Cited

U.S. PATENT DOCUMENTS 5,569,458  10/1996  Greenberg ........................ 424/195.1

*Primary Examiner*—David M. Naff
*Assistant Examiner*—Janet M. Kerr
*Attorney, Agent, or Firm*—Michael I. Kroll

[57] ABSTRACT

A composition for treating impotence in human males is disclosed, which includes a mixture of lyophilized roe and a dry powdered extract from leaves of Ginkgo biloba. The lyophilized roe is obtained from a species of Sturgeon. The dry powdered extract is standardized to include flavonoid glycosides and terpenes. The mixture preferably provides lyophilized roe to lyophilized Ginkgo biloba in the ratio of approximately 12.33:1. The composition is preferably encapsulated and orally given to patients. A process for producing the composition is also provided.

11 Claims, 1 Drawing Sheet

CONFIDENTIAL

Name _____ Color Code _____
Age _____
Job _____
Health Condition  ☐ Poor    ☐ Average    ☐ Good
Telephone & Address _____

Date Started Treatment: _____
Marital Status  ☐ Married  ☐ Single
Other Medications Taken: _____

☐ Diabetic    ☐ High B.P.    ☐ Heart Cond.

|  | Before Treatment | After 3 Weeks | 8 Weeks | 12 Weeks | 16 Weeks | 20 Weeks |
|---|---|---|---|---|---|---|
| LIBIDO (DESIRE) | WEAK ☐ AVERAGE ☐ GOOD ☐ | SAME ☐ BETTER ☐ EXCELLENT ☐ | SAME ☐ BETTER ☐ EXCELLENT ☐ | SAME ☐ BETTER ☐ EXCELLENT ☐ | SAME ☐ BETTER ☐ EXCELLENT ☐ | SAME ☐ BETTER ☐ EXCELLENT ☐ |
| ERECTION | WEAK ☐ AVERAGE ☐ GOOD ☐ | SAME ☐ BETTER ☐ EXCELLENT ☐ | SAME ☐ BETTER ☐ EXCELLENT ☐ | SAME ☐ BETTER ☐ EXCELLENT ☐ | SAME ☐ BETTER ☐ EXCELLENT ☐ | SAME ☐ BETTER ☐ EXCELLENT ☐ |
| # OF ACTUAL INTERCOURSE WEEKLY | *ONCE ☐ TWICE ☐ 3 TIMES ☐ 4> ☐ | ONCE ☐ TWICE ☐ 3 TIMES ☐ 4> ☐ | ONCE ☐ TWICE ☐ 3 TIMES ☐ 4> ☐ | ONCE ☐ TWICE ☐ 3 TIMES ☐ 4> ☐ | ONCE ☐ TWICE ☐ 3 TIMES ☐ 4> ☐ | ONCE ☐ TWICE ☐ 3 TIMES ☐ 4> ☐ |

*OTHER NOTES: IF LESS THAN ONCE A WEEK, CHECK ONCE BOX AND WRITE DOWN THE PERIOD IN LARGE BOX ACROSS.

FIGURE 1

MEDICATION FOR IMPOTENCE CONTAINING LYOPHILIZED ROE AND A POWDERED EXTRACT OF *GINKGO BILOBA*

BACKGROUND OF THE INVENTION

1. Field of the Invention

The instant invention relates generally to a medication for impotence that relieves erectile dysfunction and enhances a man's sexual desire.

2. Description of the Prior Art

Therapies currently known to the prior art include the following, along with the various known drawbacks associated with each such therapy:

1. ANDROGENS

Testosterone and its derivatives are obtained only by prescription. They are available as injection, oral, buccal tablets or other pharmaceutical dosage forms; the main use is for hypogonadism, male climactric and impotence. Testosterone also has other applications in medicine. As with other hormonal treatments, during administration of exogenous testosterone, endogenous testosterone release is inhibited through the negative feedback mechanism of the pituitary lutenizing hormone (LH.)

Large doses of exogenous androgens may suppress spermatogenisis through the negative feedback of inhibition of pituitary follice stimulating hormone (FSH.) This results in inadequate endogenous testosterone production once exogenous testosterone is discontinued.

Testosterone and its derivatives have been used successfully to develop or to maintain sexual characteristics and other physiologic functions in androgen deficient males. However it is of no benefit to patients that are not androgen deficient as can be demonstrated by plasma testosterone levels.

2. YOHOMBINE HCl

Yohombine is an indolalkylamine alkaloid. It is the principal alkaloid of the bark of the west African Coryanthe Yohimbe tree. Its effect on the peripheral autonomic nervous system is to increase parasympathetic (cholenergic) and decrease sympathetic (adrenergic) activity.

In male sexual performance, erection is linked to cholenergic activity which theoretically results in an increased penile blood inflow, decreased penile blood outflow or both causing erection without increasing the sexual desire. Yohombine is available only by prescription and is known commercially by different brand names. There are some products in the market made from powdered yohimbe bark in different dosage forms available over the counter which do not contain sufficient yohimbine alkaloid, and are not as effective as those obtained by prescription.

Yohombine has been successfully used to treat some impotent patients, specifically those suffering from diabetes.

Some of the main drawbacks of yohombine, is that it cannot be used in patients with renal disease, cardio renal disorders, gastric or duodenal ulcerations, psychiatric and geriatric patients. Side effects may include increase in the heart rate and the blood pressure.

3. PAPAVERINE

Papaverine injection is only available by prescription; generally it is not the drug of choice for many patients. Papaverine has been used as an injection administered into the penis directly. Erection usually occurs in 5-15 minutes after injection. Papaverine injection causes pain and bruising at the site of injection. Persistent painful erection that occurs independently of sexual desire (priapism) is a side effect could last from 5-7 hours causing embarrassment and discomfort to the patient. Fibrous growth in the penis tissue has also been reported.

4. CAVERJECT

Caverject is a brand name marketed and available only by prescription. It is the synthetic version of alprostadil (prostaglandin E) which the body uses to help produce an erection. The medication is to be injected directly into the penis shortly before intercourse. It relaxes smooth muscle tissue in the penis which in turn enhances blood flow to the penis and causes erection. Caverject is often effective for men whose impotence is due to diabetic complications, anxiety or radical prostatectomy. One of the major drawbacks of caverject is that the subject, after injection, may have long lasting painful erection (priapism), which may last more than 6 hours and cause serious and permanent damage to the delicate spongy structure of the penis which may never again function properly.

5. PENILE IMPLANTS

Penile implants, primarily made from silicone rubber, are surgically inserted in the shaft of the penis to make it sufficiently rigid for vaginal intercourse. Penile implant operations were first preformed in the 1960's and now some 30,000 men have the surgery each year. Penile implants come in different styles and sizes; semi-rigid, flexible rods, or cylinders that are surgically inserted into both sides of the penis but do not get as hard as a natural erection. Men with this kind of implant have permanent enlargement.

6. INFLATABLE IMPLANTS

Inflatable implants are another type of penile implants. They consist of twin cylinders connected to a pump and fluid filled reservoir. The cylinders are inserted in the penis, the pump may be concealed in the scrotum and the reservoir goes into the abdominal cavity. When you squeeze the pump you obtain an erection and when you squeeze again the erection goes away.

Implants have their own drawbacks, they are uncomfortable, require surgery which may have serious complications, are very expensive, and not every man is a candidate for penile implantation, also men look for less invasive remedies.

7. MARIJUANA

Some people think marijuana use will cause sexual stimulation, however marijuana is a sexual depressant and causes damaging effects on the brain, it is also illegal to possess or use.

8. ALCOHOL

Alcohol is also perceived as a sexual stimulant but is actually a sexual depressant and results in liver damage when consumed in quantity.

9. AMYL NITRATE

Amyl nitrate has been used (as an inhalant) because of its peripheral vasodilatation effect which is perceived as a sexual stimulant, but actually is not.

Its side effects are of serious concern particularly in men and women with hypertension or over the age of 40.

SUMMARY OF THE INVENTION

It is, therefore, an object of the present invention to provide a medication for impotence which will achieve positive effects on the libido and the penile erection, both of which are necessary to result in successful copulation.

An additional object is to reinstate self-confidence in the patient by successfully treating his impotence.

It is an object of the present invention to provide a medication to treat impotence that is safe, effective, and easy to administer with the minimal or no side effects.

It is still a further object of the present invention to provide a medication for impotence that will overcome the short-comings of the prior art through a more holistic approach that emphasizes the synergistic action of the two ingredients, lyophilized roe and ginkgo biloba powdered extract.

It is yet a further object of the invention to provide a product that has a synergistic effect that will dramatically improve the sexual activity of the man.

Another object is to provide a method for preparing the medication for impotence by lyophilization of fresh Roe and blending it with ginkgo biloba dry powdered extract standardized to 24% glycosides and 6% terpenes. The mixture is then to be packed in hard gelatin capsules for oral use.

An additional object of the present invention is to provide a method for isolating the active ingredients of Roe, for use as a pharmaceutical product as an aphrodisiac mediation, by either obtaining a dry Roe powder via air drying or via a method employing organic solvents.

A further object of the present invention is to provide a product comprised of natural constituents that will serve the purpose of solving the dilemma of impotence without using harsh devices or causing any damage or serious side effects to the body.

A final object is to provide a medication for impotence that is economical in cost both to the manufacturer and to the patient.

The foregoing and related objects are accomplished by a process in which fresh roe from sturgeon, which is available commercially in the market as caviar, is lyophilized to remove moisture. It is then ground into a homogeneous powder and blended with ginkgo biloba leaves dry powder extract standardized to 24% flavonoid glycosides and 6% terpenes, which is also available in the U.S. market sold as a dry powder with the required concentration of the flavonoid glycosides and terpenes. The blend is readily prepared using art recognized principles and methodologies in combining the ingredients together. A suitable pharmaceutical dosage form is used to administer the powdered mixture. The mixture is packed into hard gelatin capsules size (00). The mixture comprises the following ingredients by percentage:

lyophilized roe 92.5%
ginkgo biloba leaves dry extract 7.5%

Each capsule size (00) preferably contains by weight, 370 mg of lyophilized roe, and 30 mg ginkgo biloba leaves dry powdered extract. The mixture may, preferably, also comprise the following preservatives, sodium benzoate, methyl paraben and propyl paraben.

The recommended dosage for subjects suffering impotence is 4 capsules daily.

It has been found that a synergistic aphrodisiac effect can be obtained by oral use of a medication comprising a blend of lyophilized roe and ginkgo biloba leaves dry powder extract standardized to 24% flavonoid glycosides and 6% terpenes.

More than 280 studies have been published on ginkgo biloba since the 1950's, covering areas concerning the pharmacological and therapeutic effects of ginkgo biloba extract on the vascular tissue, impotence, and memory dysfunction. Gingko biloba has been researched for its effect in treating patients suffering from erectile dysfunction and several studies have been published in this area.

The synergistic effect of the blend of ginkgo biloba extract and lyophilized roe was unexpected.

Roe is commercially known as caviar and is consumed primarily as an appetizer and never thought to have such a synergistic effect with gingko biloba extract on man's sexuality.

BRIEF DESCRIPTION OF THE DRAWING FIGURE

FIG. 1 is a sample of the questionaire used in the double-blind placebo controlled studies conducted for testing the effectiveness of the medication of the present invention.

DETAILED DESCRIPTION OF THE PREFERRED EMBODIMENTS

A detailed description is herein given of the present invention as a medication for impotence comprising the lyophilized roe of any Sturgeon species. Lyophilized roe blended with ginkgo biloba leaves dry powdered extract standardized to 24% flavonoid glycosides and 6% terpenes. Roe (i.e., caviar), the eggs of sturgeon, is generally a product too esoteric to appeal to the popular taste. It is prepared by removing the egg masses from freshly caught fish. Four to six percent salt is added to preserve the eggs and bring out the flavor. It is kept refrigerated or, for better storage, it is pasteurized. Most caviar is produced in Russia and Iran from fish taken from the Caspian and Black Seas and sold in U.S. market.

Caviar is graded according to the size of the eggs and manner of processing, grades are named for the type of Sturgeon from which the eggs are taken. Beloga, the largest, is black or grey, the smaller, Osetrova, is grayish, grayish green or reddish brown. Caviar has been consumed as an appetizer for several generations. Caviar contains approximately 36–79% moisture; 2.7–3.4% protein; carbohydrates 3–5%; and, 0.01–0.05% mineral matters. Approximately 32 elements can be detected in caviar some of which are calcium, phosphorus, zinc, copper, and iron. Certain vitamins are also detectable such as vitamins A, E, riboflavin, niacin, B6, calcium pantothenate, and B12. One to 1.7% fat in the form of phospholipids; 70% of the whole lipids are unsaturated fatty acids. Most of these phospholipids occur either as phosphatidyl cholines (lethicins) or as phosphatidyl ethanolamin (cephalins), and to a lesser extent inositol phosphatides, cerebrosides and sphingomyelines.

Phospholipids play an essential role in message transmission between the nerve cells in our body. The phosphorus component helps keep nerve cells healthy, the phosphatidyl choline component assists in mental recuperation and helps increase mental activity.

In this study the invention was found to have an aphrodisiac effect on both men and women. We belive that this product has an effect on glands that control the secretion of sex hormones.

Without the proper levels of sex hormones the person will lose interest in sexual activity. It is believed that the connection between using the mediation of the present invention and increased sexual activity is that the claimed composition may be stimulate certain glands to secrete sex hormones. In all likelihood, the present invention stimulates the pituitary gland and other glands that control the secretion of sex hormones in both sexes.

For thousands of years the leaves of the ancient ginkgo tree (from the ginkgo biloba family, ginkgoaceae) have been recognized for their benefits in geriatric patients. It has been used in Chinese and Japanese medical practice for nearly 3,000 years.

Clinical and pharmacological studies have been published on ginkgo biloba leaves dry powdered extract standardized to 24% flavonoid glycosides and 6% terpenes. The most interesting and important studies relate to vascular disease, brain function, impotence, dopamime synthesis, inflammation, and asthma. Ginkgo extract also function as an antioxidant, a free radical scavenger, which helps prevent cell damage. Published clinical researches have shown that an extract from ginkgo leaves achieves vasodilation and improved blood flow especially in deeper seated medium and small arteries.

The increased flow rate in capillary vessels and end arteries resulting from ginkgo extract produces beneficial effects on the mental efficiency of elderly patients showing mild to moderate memory impairment of organic origin.

In 1989, a study was published on sixty patients suffering from arterial erectile dysfunction who had not responded to papaverine injection, the drug of choice for their condition. The subjects received a daily treatment of 60 mg of an extract of Ginkgo biloba and after 6 months, 50% of the subjects once again were able to achieve penile erections and upwards of 45% of the remaining subjects showed some improvement.

In the present extracts of ginkgo leaves are widely recommended in the Asian and European medical communities and account for annual sales of approximately $500 million. In fact, during 1988 physicians in Germany wrote more prescriptions (5.4 million) for Ginkgo biloba extract than any other drug. It is also available in Europe and Asia as an over the counter drug (OTC).

Ginkgo biloba extract is produced from the green picked leaves of the ginkgo tree grown on plantations in the United States, France, Japan, and South Korea that have been specifically developed for pharmaceutical purposes. After drying and milling, the leaves are extracted with an acetone water mixture under partial vacuum. The organic solvent is then removed and the extract processed, dried, and standardized. Ginkgo dry powdered extract is then adjusted to a potency of 24% flavonoids (mostly flavonoid glycosides and quercetin) and 6% terpenes (principally a unique group of diterpenes known as ginkgolides and ginkgo bilobalides.)

Ginkgo extract is also available as standardized 24% flavonoids and 4% terpenes. The product is marketed in the U.S. in both dry powdered and liquid form. Ginkgo tablets and capsules for oral use are also available in U.S. health food stores and pharmacies. The recommended dosage is 1 tablet 3 times daily with meals of the 40 mg standardized extract of ginkgo.

Extremely large doses of ginkgo tablets may cause restlessness, diarrhea, nausea, vomiting and other unpleasant effects, if this occurs patients are advised to reduce the dosage or stop use completely.

A preferred embodiment of the present invention may be prepared as follows:

10.0 kg of fresh roe obtained from Sturgeon species cyclopterus lumbus was lyophilized at 0.001 torr and −40° C. to remove the moisture. At completion of the drying process 2.245.5 g of dry powdered roe was obtained. The dry fluffy reddish brown powder was ground in a mill to obtain fine homogeneous powder. In a mixer 182.06 g of Ginkgo biloba leaves dry powdered extract standardized to 24% flavonoid glycosides and 6% terpenes was mixed with the powdered dry roe. The 2.4 g propyl paraben, 3.6 g of methyl paraben, and sodium benzoate which was originally included with the fresh roe as a preservative will have a satisfactory concentration in the final product. The blend is readily prepared using the geometric dilution method and art recognized principles and methodologies in combining the ingredients together to assure a homogeneous and uniformly prepared mixture.

The mixed powders are finally weighed and packed into hard gelatin capsules of suitable sizes to accommodate 400 mg of the powdered mixture (size 00) ready for oral use. The recommended dosage of this product for the treatment of impotence is 2 capsules in the morning and 2 capsules in the evening after meals. This treatment regimen should be continued until optimum results are achieved which usually takes 3–6 months.

Two further procedures, within the scope of the present invention for obtaining dry roe or its active ingredients, employ either an air drying procedure or the use of organic solvents.

A method for obtaining dry powered roe for use as a pharmaceutical product as an aphrodisiac medication, comprises the following steps: 10.0 kg of accurately weighed Sturgeon Roe is evenly spread into ¼ inch thick layers on stainless steel trays. The trays should be kept in a closed temperature controlled room between 69°–75° F. The trays are then exposed to a steady airflow from six fans, operated continuously. After 24 hours, the sample on the trays is mixed and re-spread into ¼ inch thick layers. This mixing and re-spreading process was repeated every 24 hours for 72 hours. After 72 hours, the sample product was completely dry. The large dry granules obtained were ground in a mill to a fine powder and then sieved, ready for encapsulation. The moisture content of this product ws 5.1% after fan drying, as discussed above. The net weight of the dry powdered roe obtained from 10.0 kg fresh roe was 2.283 kg.

A method within the scope of the present invention for isolating the active ingredients of roe for use as a pharmaceutical product as an aphrodisiac medication, via the use of organic solvents, comprises the following steps:

Transfer 20.0 g of accurately weighed dried roe powder in a 500 ml glass stoppered conical flask; add 100.0 ml ether; insert a stopper tightly; and, shake the flask for 30 minutes. Allow the powder to settle, then filter with suction through a fine porosity centered glass, then filter into a small filter flask. Transfer the filtered extract into a larger conical flask of suitable size (completely dry and clean) and accurately weigh empty before use.

Repeat the extraction with two-50.0 ml portions of ether; adding the filtered etherial extract each time to the conical flask; and, evaporate the etherial extract in an electric water bath. Repeat the same extraction procedure with the same sample of roe using 100.0 ml chloroform. All the chloroform filtrate to the same conical flask. Repeat the extraction using two 50.0 ml portions of chloroform, adding the filtrate each time to the conical flask; and, evaporate the chloroform.

Repeat, again extracting the same sample of roe, using acetone following the same procedure, as outlined above (100.0 ml acetone for the first extraction, then two-50.0 ml portions of acetone, adding the filtered extracts each time to the conical flask, and removing the acetone by evaporation in the hot water bath.)

The last extraction is carried out using 100.0 ml of 70% ethyl alcohol; followed by another two-50.0 ml portions of 70% ethyl alcohol; adding the filtrate each time to the conical flask; and, evaporating the solvent. Complete the evaporation of the solvents until the residue is completely dry.

The total residue obtained from all the extracts is then dried and weighed. The total dry residue, extracted by ether, chloroform, acetone and 70% ethyl alcohol, was 5.79 grams; the dry residue being the active ingredients in roe which are responsible for producing the aphrodisiac effect.

The residue is ground to a fine powder, mixing it with a suitable diluent, e.g., lactose, and then encapsulated. The equivalent dose of the residue, i.e., the active ingredients of the roe, to the original whole dry powdered roe is 0.115 gram (115 mg dry residue equivalent to 400.0 mg whole dry powdered roe.)

The foregoing methods described for extracting roe, either via air drying or utilizing organic solvents, are intended to be illustrative of such methods. Clearly, those skilled in the art will recognize that modifications to be procedures described above can readily be undertaken. All such obvious modifications should be understood as being within the scope of the present invention.

In double-blind placebo controlled studies, the medication composition of the present invention was tested on 30 human males ages 40–57, primarily suffering for impotence. Most of the subjects also suffered other medical problems including diabetes and hypertension.

All subjects were screened for their sexual activity before the trial (their penile erection capability, libido, and the number of sexual intercourses acts as shown in the attached exhibit, designated as FIG. 1.) The majority of the subjects were only able to engage in successful copulation 0–2 times/month.

The subjects were divided into three groups. The first group was given only placebo (400 mg lactose filled gelatin capsules.)

The second group was given only lyophilized roe (370 mg and 30 mg lactose in gelatin capsules.) The third group was given the composition of the invention (370 mg lyophilized roe and 30 mg Ginkgo biloba extract in gelatin capsules.) The studies were conducted for three months.

The first placebo group showed very little response; the average sexual activity increased by approximately 11%. The second group, which received the roe extract only, manifested an increase in the average monthly sexual activity by approximately 49%. The third group, which was received the combination product (370 mg roe and 30 mg Ginkgo), showed a significant response compared to the first and second groups. The third group showed an average increase in their monthly sexual activity by 87%. It was also noted that some subjects in the third group showed a moderate improvement in penile erection ability and sexual desire in as little as three weeks after the start of the treatment.

In another study it was noted that male subjects with normal sexual activity (engaging in copulation 7–9 times per month) who were given the product used in the 3rd group above showed an average of 52% increase in their sexual activity (10–12 times/month) after six weeks of therapy.

No side effects were detected during the trial period, except for one subject who exhibited a mild allergic reaction.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A composition for treating impotence in human males, comprising a mixture of lyophilized roe and a dry powdered extract from leaves of *Ginkgo biloba*, said lyophilized roe being obtained from a species of Sturgeon and said dry powdered extract being standardized to include flavonoid glycosides and terpenes, said mixture comprising lyophilized roe to dry powdered Ginkgo biloba extract in a ratio of approximately 12.33:1.

2. The composition for treating impotence in human males according to claim 1, wherein said lyophilized roe comprises approximately 92.5% of said mixture and said dry powdered extract comprises approximately 7.5% of said mixture, said dry powdered extract being standardized to approximately 24% flavonoid glycosides and 6% terpenes.

3. The composition for treating impotence in human males according to claim 1, further comprising pharmacologically compatible preservatives.

4. The composition for treating impotence in human males according to claim 1, wherein said mixture includes approximately 30 mg of lyophilized Ginkgo biloba and 370 mg of lyophilized roe.

5. The composition for treating impotence in human males according to claim 1, further comprising a capsule into which said mixture is packed for administration to a patient.

6. The composition for treating impotence in human males according to claim 1, further comprising a member selected from the group consisting of an alkaloid, a hormone, a vitamin, a phospholipid, an amino acid, calcium, zinc, selenium, melatonin, an anti-oxidant, a bioflavonoid and a combination thereof.

7. The composition for treating impotence in human males according to claim 6, wherein said alkaloid is yohimbine or a derivative thereof.

8. The composition for treating impotence in human males according to claim 6, wherein said hormone is testosterone or a derivative thereof.

9. The composition for treating impotence in human males according to claim 6, wherein said vitamin is a member selected from the group consisting of Vitamin A, Vitamin C, Vitamin E and a combination thereof.

10. A process for producing a composition for treating impotence in human males, including a mixture of lyophilized roe and a dry powdered extract from leaves of Ginkgo biloba, said lyophilized roe being obtained from a species of Sturgeon and said dry powdered extract being standardized to include flavonoid glycosides and terpenes, said process comprising the steps of:

removing moisture from roe to obtain a dried lyophilized roe; and, blending the dried lyophilized roe with a dry powdered extract from leaves of Ginkgo biloba by geometrical dilution, wherein said blending step results in a blend comprising lyophilized roe to dry powdered Ginkgo biloba extract in a ratio of approximately 12.33:1.

11. The process for producing a composition for treating impotence in human males according to claim 10, further comprising the step of encapsulating said composition into a gelatin capsule.

* * * * *